United States Patent [19]

Morganroth

[11] 4,116,365

[45] Sep. 26, 1978

[54] METHODS OF PREPARING BLEACH PASTE FOR AND APPLYING IT TO HAIR

[76] Inventor: Shila Morganroth, 1225 Waterbury Rd., Highland, Mich. 48031

[21] Appl. No.: 688,596

[22] Filed: May 21, 1976

Related U.S. Application Data

[60] Division of Ser. No. 579,012, May 19, 1975, which is a continuation-in-part of Ser. No. 481,695, Jun. 14, 1974.

[51] Int. Cl.$^2$ ............................................. B65D 35/44
[52] U.S. Cl. ................................... 222/92; 132/7
[58] Field of Search ................... 222/1, 94, 190, 92; 132/7, 11 R, 33, 1 R; 141/114; 259/72

[56] References Cited

U.S. PATENT DOCUMENTS

| | | | |
|---|---|---|---|
| 2,133,638 | 10/1938 | Singerman | 132/7 |
| 2,939,615 | 6/1960 | Lerner | 132/7 X |
| 3,015,386 | 1/1962 | Maynier et al. | 132/1 R X |
| 3,261,381 | 7/1966 | Roach | 141/114 |
| 3,596,801 | 8/1971 | Barnack | 222/94 X |
| 3,651,990 | 3/1972 | Cernei | 222/94 |

FOREIGN PATENT DOCUMENTS

| | | | |
|---|---|---|---|
| 1,301,903 | 1/1973 | United Kingdom | 132/7 |

*Primary Examiner*—Stanley H. Tollberg
*Attorney, Agent, or Firm*—George H. Mortimer

[57] ABSTRACT

A method of preparing bleach paste of bleach powder fine enough to cause a dust problem and a liquid developer which comprises prepackaging the dusting powder in unit quantity in a flexible plastic bag having an opening in the wall thereof that may be closed, introducing liquid developer into the bag through the opening in quantity sufficient to form a paste of desired consistency when thoroughly mixed, and mixing the powder and liquid by manipulating the bag while maintaining the opening closed to prevent the escape of dust into the atmosphere. The paste may then be dispensed directly from the opening onto hair to be bleached thereby.

This method of applying bleach directly onto the hair from a flexible bag through a suitable opening may also be carried out if the paste is prepared in ways other than manipulating a bag that contained a prepackaged unit quantity of bleach powder. Thus, the bag is first provided with a quantity of the bleach paste, whether by manipulation of prepackaged powder with developer or by introduction of paste prepared outside the bag, then pressure is applied outside the bag, e.g., by squeezing it, to extrude paste from it through a discharge orifice. The discharged paste is applied directly onto the hair. The spreading of the paste on the hair may be assisted by a penetrating spreading means such as a brush or a comb.

2 Claims, No Drawings

METHODS OF PREPARING BLEACH PASTE FOR AND APPLYING IT TO HAIR

This application is a division of my application Ser. No. 579012 filed May 19, 1975 as a continuation-in-part of my prior application Ser. No. 481,695 filed June 14, 1974.

INTRODUCTION

The present invention relates to methods of preparing bleach paste for use in altering hair color selectively and to methods of applying bleach pastes to hair from flexible and compressible containers used in these methods. The methods of altering hair color selectively in which the methods of the invention find application include hair highlighting; hair painting; and hair streaking with a viscous liquid bleach; hair shading; hair frosting; hair tipping and the like. The word "liquid" as used herein is intended to be broad enough to include any spreadable material even if it will not flow readily because of high viscosity.

BACKGROUND OF THE INVENTION

Powdered bleach materials are known in the hair coloring art which, when mixed with a developer such as hydrogen peroxide of various strengths or "volumes", can be applied to the hair as an "off-the-scalp" type bleach. It is so called because many persons have skin that is irritated by contact with the bleach material. Hair can also be damaged by improper use of the bleach material. Because of the nature and properties of powdered bleach materials, such as BASIC WHITE, special packaging for intended uses have been customarily used and special instructions for mixing and applying the materials have been issued by the manufacturers of such products.

For example, BASIC WHITE, is a very fine powdered material that is hygroscopic and therefore must be protected against humidity in the atmosphere during storage. It requires the admixture with it of a developer, generally a peroxide solution, in order to form a paste which is in a condition for spreading on the hair by a brush in the manner described hereinabove. The current practice as exemplified by a kit for frosting or tipping a woman's hair is to produce and seal a carton containing a bowl or mixing vessel, an air-tight can of BASIC WHITE, a plastic squeeze bottle containing the developer and having a moisture-tight cap screwed on the neck thereof, a spoon or the like to serve as the mixing implement when the powder and the developer are mixed together in the open bowl, a perforated cap, two plastic hooks and a sheet of instructions with a double sheet of plastic adhering to the back side in which a pair of gloves is formed by heat sealing the periphery and weakening the sheet around them so that the gloves can be pulled loose to wear during application of the mixture of the BASIC WHITE and developer to the hair pulled through the perforations in the cap. The instructions warn against inhaling the personally obnoxious cloud of powder which inevitably rises from the mixing bowl when the can is emptied into it and when the powder is first stirred to blend it with the liquid developer. The paste is usually applied to the hair by means of a brush, either all over or selectively in streaks, as in hair painting where regular, uniform strands of hair are painted by a brush that is dipped into the paste in the bowl and then moved downwardly, starting with the paste about ⅛ inch away from the scalp and continuing to the ends of the hairs in the strand.

In another current practice for beauty shop use, BASIC WHITE is sold in much larger quantity than the aforementioned unit size needed for a single hair treatment. Currently the larger quantity of powder is placed in a single plastic bag large enough to hold the same and this bag is put inside a can that may be opened and closed to minimize contact of the atmosphere with the BASIC WHITE until it has all been used up by removing successive unit quantities, mixing each unit quantity with developer in a bowl and then using it. The problem of dust in the air attends the use of the powder when packaged and mixed in this way also.

SPECIFIC EMBODIMENTS OF THE INVENTION

The present invention overcomes these difficulties of the prior art by prepackaging a unit quantity of bleach powder in a thin, moisture-resistant plastic container, i.e., just sufficient for a single application for the purpose for which the package is intended, introducing developer liquid into the bag through an opening, and mixing them by manipulating or kneading the bag and contents. As used herein the term "mixing them by manipulating or kneading the bag and contents" means to press upon the outside of the bag with the thumb and fingers where the powder and developer liquid are present within to work or press or knead them into a homogeneous pasty mass. The passageway or opening through the wall of the bag is large enough to admit the introduction of the liquid to be mixed with the powder and also large enough for discharge of the pasty product resulting from the mixing of the powder and the liquid developer. The plastic bag, after receiving its charge of BASIC WHITE powder, may be closed in any desired way to avoid spillage of the powder in normal handling between filling and use. It is placed within a can which may be of either type presently used for shipping BASIC WHITE described above, i.e., of the single-use type for home use and the multiple-use type for beauty salons. The present invention contemplates use of the plastic bags in packages comprising cans of both types, i.e., a smaller type containing the single charge of powder in the plastic bag and a larger type containing many such bags which may be removed one at a time for use in a beauty salon according to the method of the present invention.

A package for a single use in the home preferably comprises a carton, a can containing the powdered bleach, e.g., BASIC WHITE, in a plastic bag, a bottle of developer and optionally a cap, gloves and instructions but it is not necessary to include the other implements normally contained within such a package, e.g., the mixing spoon and the mixing bowl, because the bag itself serves as the mixing vessel.

A package for multiple use in a beauty shop comprises a can with a tight lid, e.g., a press-type lid, that can be pried out with a lever to make the individual bags available for removal for use in the manner described and then pressed back in the opening to minimize free contact of the atmosphere with the interior. In the can are many bags of the structure described herein, each containing a unit quantity of the bleaching powder. Developer may be separately packaged in single or multiple use containers.

If desired, the flexible-walled plastic bag used in the process of the invention may have a reinforcing ring secured thereto around the opening. Such a ring has benefits in application of the paste to the hair in a number of different ways, e.g., by brush and by extrusion through an orifice directly onto the hair. Thus a ring around the opening makes access to the bag by a brush easier than if the opening is simply a hole in the wall of the bag. Also such a ring may be threaded to receive selectively (a) simple closure cap, (b) a cap that may be opened and closed by a pivoted tip having a discharge passageway through it, or (c) a cap having a discharge orifice. The discharge passageway and orifice in caps of type (b) and (c) are of a size permitting a stream or ribbon of BASIC WHITE paste to be dispensed through them when pressure is exerted on the bag directly onto the hair for hair painting, streaking, frosting, tipping and the like. The caps of types (b) and (c) may include a brush adjacent to the discharge orifice to assist in painting the paste on the hair. When a dispensing cap of type (c) is used, the bag is preferably closed for transportation by a simple closure cap and the threaded dispensing fixture or cap is included in the package to replace the closure cap for dispensing the paste. Just prior to use of the unit quantity of powder in a plastic bag of any of these types, the developer is introduced through the opening in the wall thereof into the bag where the powder is contained, which does not create any dust problem whatsoever. The opening is then closed in any satisfactory way, e.g., by twisting the upper end of the bag, by use of a closure cap or a valve cap, or by use of a cap with an open discharge orifice that is closed by a finger of the hand of the person who is mixing the ingredients, etc., while the contents of the bag are manipulated or kneaded so as to effect thorough mixing. Since the mixing takes place in an air tight environment, no dust problem, spillage or the like occurs during the mixing and every bit of the original powder in the bag may be properly admixed with the developer. After manipulating the flexible-walled package sufficiently to effect thorough mixing, the pasty product produced in the mixing operation can be taken out of or expelled from the plastic bag for use in any desired way, e.g., for spreading on the palms of the hands to produce natural highlights, as described in the aforesaid parent application, or it may be removed on a brush for applying to the hair to effect streaking, or it may be squeezed from the bag through the discharge orifice directly onto the hair for painting or into a bowl for any use to which such paste has been put heretofore.

The method of painting or streaking hair by squeezing a paste from a flexible bag through a discharge orifice directly onto the hair is not restricted to plastic bags of the types described above in which the paste is prepared in the bag by manipulation but can also be carried out by means of other devices which can be filled with paste of suitable consistency that has been mixed elsewhere, e.g., in a bowl. An ordinary squeeze bottle with a cap having a discharge orifice of proper dimensions is an example of such a device. A pastry bag such as is used for decorating cakes with icing is another example of such a device. A pastry bag typically is a funnel shaped fabric bag having a discharge orifice with small end in which variously shaped nozzles can be placed from within and a filling opening in the large end through which the material to be extruded through the small end can be introduced by a spoon or the like. After a desired amount of the extrudable material has been put into the bag, the large end is closed by folding it over and holding it in this position as the bag is squeezed to extrude the material through the discharge orifice at the small end. The method of painting or streaking hair in accordance with this embodiment of the invention contemplates the use of any device which can hold a charge of hair treating paste, wherever the paste may have been prepared, and dispense it as a stream suitable for direct application to the hair to be painted or streaked.

The foregoing specific examples of the methos of invention are illustrative of the principles of the invention set forth hereinabove and in the following claims are not to be construed as restricting the scope of the invention to the specific procedures of the examples.

Having thus described and illustrated the invention, what is claimed is:

1. A method of preparing a bleach paste of liquid developer and personally obnoxious dusting bleach powder which comprises prepackaging a unit quantity of powdered bleach in a flexible plastic bag having an opening in the wall thereof, said bag having a thin wall capable of being kneaded, introducing into said bag through said opening a quantity of liquid developer sufficient to convert the powder into paste of proper consistency for spreading on hair to be bleached, and kneading the bag to blend the liquid and powder into a paste while maintaining the opening in the bag closed to prevent dust from the powder escaping into the atmosphere outside the bag.

2. A method of applying a bleach paste to hair after preparing it as set forth in claim 1 in which the paste is dispensed from the bag through said opening directly onto hair to be bleached thereby.

* * * * *